United States Patent [19]

Bosshard et al.

[11] 4,323,701
[45] Apr. 6, 1982

[54] PROCESS FOR THE PREPARATION OF INDENONECARBOXYLIC ACIDS

[75] Inventors: Hans Bosshard, Basel; Hermann Rempfler, Ettingen; Hans Zweifel, Basel, all of Switzerland

[73] Assignee: Ciba-Geigy Corporation, Ardsley, N.Y.

[21] Appl. No.: 232,763

[22] Filed: Feb. 9, 1981

Related U.S. Application Data

[62] Division of Ser. No. 114,488, Jan. 23, 1980, abandoned.

[51] Int. Cl.³ .................... C07C 59/81; C07C 62/38; C07C 51/08; C07C 69/757
[52] U.S. Cl. .................................... 562/462; 560/51; 562/459
[58] Field of Search ................................ 562/462, 459

[56] References Cited

U.S. PATENT DOCUMENTS

| | | | |
|---|---|---|---|
| 3,652,716 | 3/1972 | Holub et al. | 562/462 |
| 3,729,446 | 4/1973 | Holub et al. | 562/462 |
| 3,763,271 | 10/1973 | Klebe et al. | 562/462 |
| 3,773,718 | 11/1973 | Klebe et al. | 562/462 |
| 3,985,566 | 10/1976 | Buhr et al. | 562/462 |
| 4,079,041 | 3/1978 | Baumann et al. | 562/462 |
| 4,107,174 | 8/1978 | Baumann et al. | 562/462 |

FOREIGN PATENT DOCUMENTS

| | | | |
|---|---|---|---|
| 49-128991 | 12/1974 | Japan | 562/462 |
| 49-128992 | 12/1974 | Japan | 562/462 |
| 49-128993 | 12/1974 | Japan | 562/462 |
| 50-5376 | 1/1975 | Japan | 562/462 |
| 50-5377 | 1/1975 | Japan | 562/462 |
| 50-77363 | 6/1975 | Japan | 562/462 |

OTHER PUBLICATIONS

T. Zincke et al, Ann. 283, 341 (1894).
R. E. Lutz, J. Am. Chem. Soc. 52, 3404 (1930).
G. Roberge et al, Syn. Comm. 9(2), 129 (1979).

Primary Examiner—Paul J. Killos
Attorney, Agent, or Firm—Luther A. R. Hall

[57] ABSTRACT

The invention relates to a process for the preparation of halogenoindenonecarboxylic acids of the formula

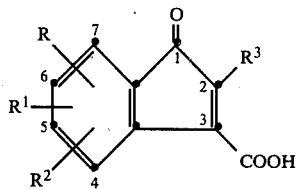

in which $R^3$ is preferably chlorine and R, $R^1$ and $R^2$ are, for example, H or $-CH_3$. If these acids are novel, the corresponding substances are claimed. The invention also relates to corresponding esters of these acids, which contain reactive end groups. The compounds are suitable for the preparation of light-sensitive polymers.

11 Claims, No Drawings

PROCESS FOR THE PREPARATION OF INDENONECARBOXYLIC ACIDS

This is a Divisional of application Ser. No. 114,488, filed on Jan. 23, 1980, now abandoned.

The present invention relates to halogenoindenonecarboxylic acids, processes for their preparation and esters of these halogenoindenonecarboxylic acids. The halogenoindenonecarboxylic acids according to this invention are suitable for the preparation of photocrosslinkable polymers. Light-sensitive polymers based on halogenoindenonecarboxylic acids have not been disclosed hitherto and a corresponding sensitivity to light of this acid itself has also not been described.

However, a number of polymers of different types which are crosslinkable by the action of light and in which crosslinking is effected by a photocyclodimerisation of specific C=C double bonds have already been disclosed. The patent applications and patents listed below constitute the prior art, which comprises not only light-sensitive polymers of this type but also corresponding light-sensitive monomers which are suitable for the preparation of such polymers: Japanese Published Specifications: 49-128,991, 49-128,992, 49-128,993, 50-5,376, 50-5,377, 50-5,378, 50-5,379, 50-5,380, 50-9,682, 50-10,884 and 50-77,363, German Offenlegungsschriften Nos: 2,031,573, 2,032,037, 2,626,795 and 2,407,033 and U.S. Pat. No. 4,079,041.

With the exception of the polymers according to German Offenlegungsschrift No. 2,407,033, these known light-sensitive polymers are substances for which the sensitivity to light is due to maleimide groups or derivatives thereof. The sensitivity to light of the polymers according to German Offenlegungsschrift No. 2,407,033, on the other hand, is due to substituted 1-carbonyloxy-1H-naphthalen-2-one groups.

The crosslinkable polymers known hitherto have the disadvantage of a relatively low photochemical sensitivity and for this reason are not suitable or are not well suited for numerous applications for which substances highly sensitive to light are required, or, alternatively, they require the additional use of known photosensitisers, such as benzophenone, thioxanthone and the like. Moreover, these polymers are colourless. Frequently, however, for technical reasons it is desired that the light-sensitive material has a specific colour. With the known polymers, expensive dyeing is then necessary and this sometimes also results in interference.

Chloroindenonecarboxylic acid of the formula

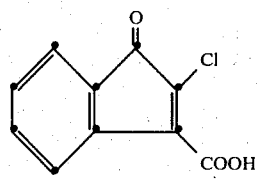

has already been described in a publication by Th. Zincke and M. Engelhardt, Annalen d.Ch. 283 (1894) 341-360.

This compound is prepared by a very involved, multi-stage process which apparently provides the product in a poor yield. It is not possible to prepare any other chloro-indenonecarboxylic acids, for example those in which H atoms of the six-membered ring in the above formula have been replaced by substituents, this lack of success presumably being due to side reactions such as oxidation.

In J.Am.Chem.Soc. 52 (1930) 3404-3422, R. E. Lutz has reported, inter alia, on the Friedel-Crafts reaction of dibromomaleic anhydride with benzene in the presence of AlCl₃. He obtained in the main resinous products of high molecular weight and, in low yield, also the bromocarboxylic acid of the formula

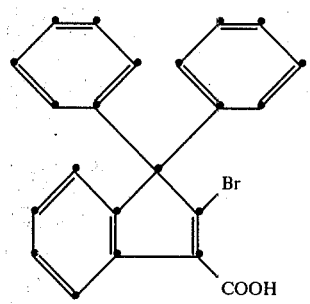

In a further publication "A convenient synthesis of some highly functionalised chromones and indones", Synthetic Communications 9 (2), 129-139 (1979), G. Roberge and P. Brassard reported on indenonecarboxylic acids which contain a OH group in the 7-position of the six-membered ring. However, these compounds are entirely unsuitable for the preparation of photocrosslinkable polymers.

The object of the invention is to find a process for the preparation of the halogeno-indenonecarboxylic acid of the formula indicated above, which process is uncomplicated and can be carried out industrially in as simple and economical a manner as possible, which results in a high yield and in a product which from the start is as pure as possible, and which further makes it possible, by changing the starting materials, also to prepare other halogenoindenonecarboxylic acids, i.e. substituted halogenoindenonecarboxylic acids. Thus, part of the object of the invention is also to provide those novel substituted halogeno-indenonecarboxylic acids which, like the unsubstituted acids, are suitable, inter alia, for the preparation of photocrosslinkable polymers.

However, the object of the invention also comprises the provision of esters of these halogenoindenonecarboxylic acids, which, in each case, contain, in the end position, a reactive group which is polymerisable and/or suitable for reaction with reactive side groups of polymers, the said esters ultimately advantageously being usable as starting materials for the preparation of photocrosslinkable polymers.

In accordance with the object of the invention, the halogeno-indenonecarboxylic acids and the corresponding esters should be starting materials for those photocrosslinkable polymers which, in respect of their characteristics, are superior to the light-sensitive polymers of the prior art. That is to say, these polymers should have a very specific characteristic colour, which is not the case with the polymers of the prior art.

At the same time, because of high characteristic absorption in long-wave UV they should crosslink easily without the use of sensitisers.

The invention relates to a process for the preparation of indenonecarboxylic acids of the formula I

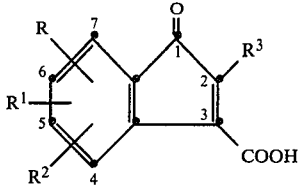

(I)

in which $R^3$ is Cl or Br, preferably Cl, and R, $R^1$ and $R^2$ are identical or different and R is a n-alkyl radical having 1 to 4 C atoms, preferably $CH_3$, or is H, Cl, Br or F, $R^1$ is a n-alkyl radical having 1 to 4 C atoms, preferably $CH_3$, or is H, and $R^2$ is H or $CH_3$, or $R^1$ and $R^2$ together are the group $-CH_2CH_2CH_2-$, in which latter case the bond to the six-membered ring is via the C atoms in the 5-position and 6-position of the nucleus, which comprises subjecting an aromatic compound of the formula II

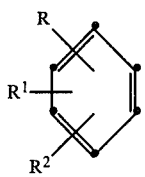

(II)

in which the H atoms on at least 2 adjacent C atoms of the nucleus have not been replaced by substituents and in which R, $R^1$ and $R^2$ are as defined for formula I, either together with a dihalogenomaleic anhydride of the formula III

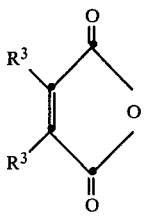

(III)

or together with an ester of the formula IV

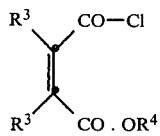

(IV)

in which formulae $R^3$ is as defined for formula I and $R^4$ is a low-molecular organic radical, especially an aliphatic radical, a cycloaliphatic radical, an aliphaticaromatic radical or an aromatic radical, in each case in an approximately stoichiometric ratio, to a condensation reaction in the presence of $AlCl_3$ and if desired in the presence of inert fluxes and/or solvents, at temperatures between 40° and 150° C., and hydrolysing the reaction product thus obtained.

The hydrolysis is advantageously effected by pouring the complex compound initially obtained by the condensation reaction into a mineral acid/water/ice mixture. In some cases, especially when the solid residue disintegrates to a powder after all of the solvents have been removed, it is also possible to effect the hydrolysis by adding dilute mineral acids, such as hydrochloric acid, to the dry product, with cooling. Preferably, the reaction according to the invention is carried out in one stage, as described above. In principle, however, the process can also be carried out in 2 stages by preparing a keto-carboxylic acid of the formula V

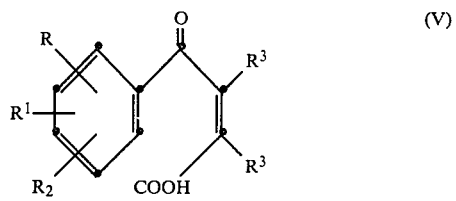

(V)

in the reaction mixture in the 1st stage, in a manner known per se, and isolating this acid and, in the 2nd stage, cyclising the ketoacid of the formula V, likewise in the presence of $AlCl_3$ and if desired in the presence of inert fluxes and/or solvents, but at temperatures between 40° and 150° C., to give the corresponding indenonecarboxylic acid of the formula I, which is liberated from the resulting reaction mixture by hydrolysis.

The reaction conditions for the 2nd reaction step thus correspond in virtually all respects to those for the 1-stage process, the only difference being that in this 2nd reaction step the intermediate of the formula V is already present, in place of the original starting materials of the formula II and III or IV.

The starting materials of the formula II and III or IV are known per se and can be prepared by conventional methods. The compounds preferably employed as the dihalogenomaleic anhydride of the formula III or as the ester of the formula IV are, in each case, those compounds which have the formulae III and IV in which $R^3$ is Cl. In principle, mixed halogen compounds which contain Cl and Br at the same time can also be used. However, as is known, these products are not as readily accessible as, for example, dichloromaleic anhydride.

A large number of compounds can be employed as the esters of the formula IV, since the radical $R^4$ can be a large number of organic groups, which are derived from corresponding alcohols and phenols.

Preferably, $R^4$ is an aliphatic radical having a total of 1 to 4 C atoms, preferably $CH_3$.

In the reaction mixture which is initially introduced for the process according to the invention, the $AlCl_3$ should preferably be present in an amount of at least 1 mol per mol of the dihalogenomaleic anhydride of the formula III or of the ester of the formula IV.

If the reaction is carried out, according to the invention, in the presence of inert solvents, which is a preferred form of the process according to the invention, the solvents or solvent mixtures to be employed are those which have a boiling point of not less than 40° C. Examples of suitable solvents are polyhalogenated aliphatic and aromatic hydrocarbons, such as o-, m- and p-dichlorobenzene, methylene chloride and 1,1,2,2,-tetrachloroethane. Nitrobenzene and dialkylamides of low-molecular carboxylic acids, such as dimethylformamide or diethylformamide, are also suitable. Solvents preferably used are 1,1,2,2-tetrachloroethane and nitrobenzene. In the case of nitrobenzene, however, the reaction temperature must be kept below 90° C. because of the danger of explosion. The dialkylamides of low-molecular carboxylic acids, preferably dimethylformamide, can also be used very effectively as solvents. The molar ratio of dialkylamide to AlCl₃ in the reaction mixture should be at least 1:1.

The use of inert fluxes is also a preferred form of the process according to the invention. Suitable fluxes are inorganic salts or organic fluxes, or mixtures of the inorganic salts with the organic fluxes. The amount of fluxes used must preferably be so chosen that the melting point which results when the fluxes are mixed with the AlCl₃ in the reaction mixture is lower than the reaction temperature. Advantageously, the amounts employed are so chosen that a lowering of the melting point results when the fluxes are mixed with the AlCl₃, for example because of the formation of a eutectic mixture.

Organic fluxes preferably employed according to the invention are dialkylamides of low-molecular carboxylic acids, for example dimethylformamide or diethylformamide. The amount should preferably be so chosen that the molar ratio of dialkylamide to AlCl₃ is between the limits 1:4 and 1:1.

Inorganic salts preferably employed are NaCl and/or KCl, if desired together with dimethylformamide as an organic flux. Further suitable inorganic fluxes (especially mixtures) can be taken from the publication by C. A. Thomas, "Anhydrous Aluminium Chloride in Organic Chemistry" (ACS Monogr. Ser.) (New York 1941).

With the process according to the invention, the particular reaction temperature and reaction time are substantially dependent on the nucleophilic reactivity of the aromatic compound of the formula II which is used. This, in turn, determines the choice of the solvent or flux. In general, the following rules apply:

(a) When reactive aromatic compounds of the formula II (which contain 2 to 3 CH₃ groups as substituents on the six-membered ring) are used, reaction temperatures of 40° to 80° C. suffice, i.e. either organic solvents or fluxes or fluxes based on, for example, NaCl/KCl can be used.

(b) When less reactive aromatic compounds of the formula II (which contain H and halogen on the six-membered ring) are used, reaction temperatures of 80° to 130° C. are required; in this case it is essential to use fluxes, especially inorganic fluxes based on an alkali metal chloride and/or alkaline earth metal chloride, or organic fluxes based on amides of lower aliphatic carboxylic acids, such as dimethylformamide.

With the rule laid down under (a), the reaction times for carrying out the reaction which are required for an economical procedure are in general between 0.5 and 12 hours. With the rule described under (b), reaction times of between 2 and 8 hours are preferably employed.

The invention also relates to compounds of the formula VI

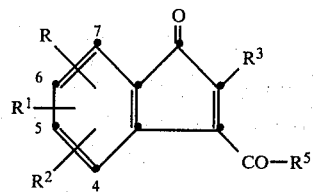

in which R³ is Cl or Br, preferably Cl, and R, R¹ and R² are identical or different and R is a n-alkyl radical having 1 to 4 C atoms, preferably CH₃, or is H, Cl, Br or F, R¹ is a n-alkyl radical having 1 to 4 C atoms, preferably CH₃, or is H, and R² is H or CH₃, or R¹ and R² together are the group —CH₂CH₂CH₂—, in which latter case the bond to the six-membered ring is via the C atoms in the 5-position and 6-position of the nucleus, and in which R⁵ is one of the radicals —OH, —O—(CH₂)ₘ—OH, —O—(CH₂—CH₂—O)ₙ—CH₂—CH₂—OH,

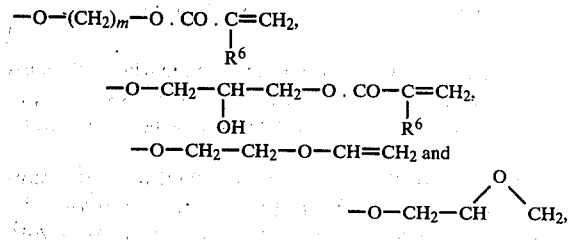

in which m is a number from 2 to 6, n is a number from 1 to 10 and R⁶ is H or —CH₃, with the proviso that if R⁵ is —OH at least one hydrogen atom in the 4-position to the 7-position of the six-membered ring has been replaced by a substituent.

Preferred compounds of the formula VI are those which have the formula VI in which R⁵ is —OH, i.e. the free halogen-indenonecarboxylic acids, especially the products containing chlorine. Corresponding preferred esters are those of the formulae VII and VIII

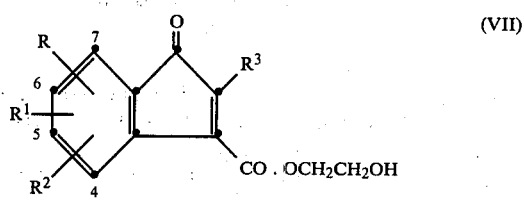

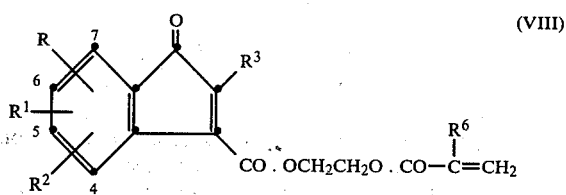

in which the indicated radicals R to R⁶ are as defined above. Preferably, R³ in formulae VII and VIII is chlorine in each case.

Particularly preferred compounds are those of the formulae XVII, XVIII and XIX:

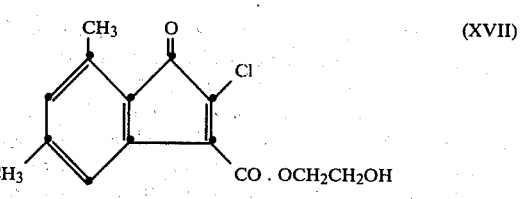

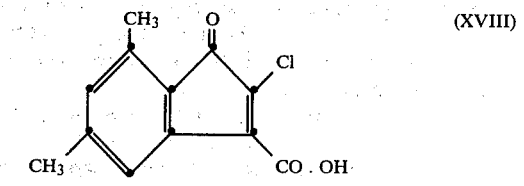

-continued

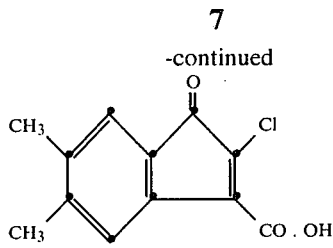 (XIX)

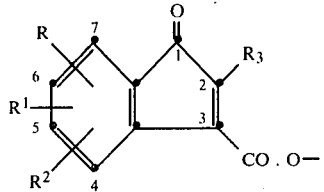 (IX)

The esters of the halogenoindenonecarboxylic acids of the formula VI are prepared by processes known per se. To be more precise, the following aspects should be mentioned in detail.

The esters of the formula VI in which $R^5$ is the radical $-O-(CH_2)_m-OH$ are prepared by esterifying the corresponding halogeno-indenonecarboxylic acid with the particular alkylene glycol in the presence of inert organic solvents (for example ethylene glycol dimethyl ether) and esterification catalysts (for example sulfuric acid).

The esters of the formula VI in which $R^5$ is the radical $-O-(CH_2-CH_2.O)_n-CH_2-CH_2-OH$ are prepared by adding n molecules of ethylene oxide onto the particular halogeno-indenonecarboxylic acid.

The esters of the formula VI in which $R^5$ is the radical

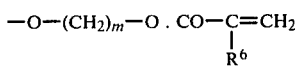

are prepared by esterifying the particular hydroxy-alkyl ester (i.e. $R^5$ is the radical $-O-(CH_2)_m-OH$) with acrylic acid or methacrylic acid.

The esters of the formula VI in which $R^5$ is the radical

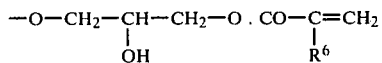

are prepared either by reacting glycidyl acrylate or glycidyl methacrylate with the particular halogeno-indenonecarboxylic acid or by reacting acrylic acid or methacrylic acid with the particular halogeno-indenonecarboxylic acid of the formula VI in which $R^5$ is the radical

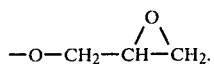

The last-mentioned product of the formula VI is prepared by reacting epichlorohydrin with the particular halogenoindenonecarboxylic acid.

The esters of the formula VI in which $R^5$ is the radical $-O-CH_2-CH_2-O-CH=CH_2$ are prepared by a condensation reaction of α-chloro-ethyl vinyl ether and the particular halogenoindenonecarboxylic acid.

In all the processes for the preparation of the halogenoindenonecarboxylic acid esters of the formula VI, the reaction is preferably carried out in the presence of inert organic solvents.

The novel, improved, photocrosslinkable polymers which can be prepared using compounds of the formula VI as starting materials contain side groups of the formula IX in which the radicals R to $R^3$ are as defined for formula I. The proportion of groups of the formula IX is 5 to 100 and preferably 20 to 100%, based on the number of recurring structural elements of the particular polymer.

These light-sensitive polymers are, for example, those from the group of the phenol-formaldehyde resins, the novolacs and the phenoxy resins and those which are obtained by homopolymerization or copolymerisation of monomers containing C=C double bonds.

The polymers can be prepared by synthesis methods which are known per se for the preparation of macromolecules containing photoactive side groups. In principle, the following routes can be employed:

1. Incorporation of the group of the formula IX in an existing polymer chain and
2. Build-up of the polymer chain from monomers which already contain the light-sensitive group of the formula IX, this build-up of the chain preferably being effected by means of polymerisation via C=C double bonds.

With the 1st method of preparation, the reaction is always carried out in the presence of inert solvents. With the 2nd method, the polymerisation is carried out either as block polymerisation or in the presence of inert solvents. Since both processes are carried out by basic methods known per se, it is superfluous here to give further data on the solvents which are to be used in some cases and on catalysts and temperatures. Basic methods of this type are, moreover, described in detail in U.S. Pat. No. 4,079,041.

In some cases, the same products can be obtained by methods 1 and 2, so that method 1 or method 2 can be used as desired. If the groups of the formula IX are incorporated into an existing polymer chain, this incorporation is effected, for example, by an addition reaction with simultaneous opening of a ring system, for example of a dicarboxylic acid anhydride group or of an epoxide group.

One possible form of these polymers is a homopolymer or copolymer of monomers containing reactive double bonds, which has average molecular weights of between 1,000 and 1,000,000 and which contains the groups of the formula IX in molecule chain members of the formulae a to e

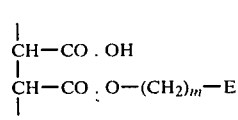 (a)

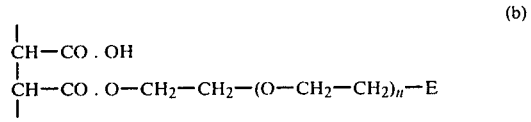 (b)

-continued

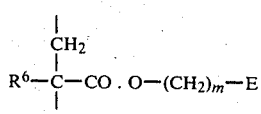 (c)

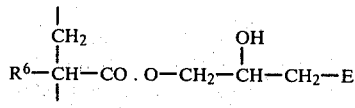 (d)

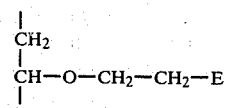 (e)

in which the radical E has the formula IX, m is a number from 2 to 6, n is a number from 1 to 10 and $R^6$ is H or —$CH_3$.

As well as containing one or more of the structural elements of the formulae a to e, a polymer of this type can at the same time contain structural elements of the formula f

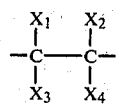 (f)

in which $X_1$ and $X_3$ are each hydrogen, $X_2$ is hydrogen, chlorine or methyl and $X_4$ is hydrogen, methyl, chlorine, —CN, —COOH, phenyl, methylphenyl, methoxyphenyl, cyclohexyl, —COO—alkyl having 1–12 C atoms in the alkyl moiety, —COO—phenyl,

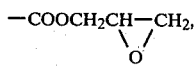

—COO—alkyl—OH having 1–3 C atoms in the alkyl moiety, —OCO—alkyl having 1–4 C atoms in the alkyl, —OCO—phenyl, —CO—alkyl having 1–3 C atoms in the alkyl, alkoxy having 1–6 C atoms or phenoxy, or $X_1$ and $X_2$ are each hydrogen and $X_3$ and $X_4$ together are the grouping

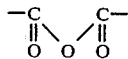

or are each —COOH or —COO—alkyl having 1–6 C atoms in the alkyl.

Amongst these particular polymers, those which are preferred are those which contain structural elements of the formula f in which $X_1$ and $X_3$ are each hydrogen, $X_2$ is hydrogen or methyl and $X_4$ is —$OCOCH_3$—, —COOH or —COO—alkyl having 1–8 C atoms in the alkyl, or in which $X_1$, $X_2$ and $X_3$ are each hydrogen and $X_4$ is —CN, chlorine or phenyl.

A further possible polymer, which can be prepared using the compounds, according to the invention, of the formula VI as starting materials, is a polymer which is based on novolac as a starting material and which contains structural elements of the formula g

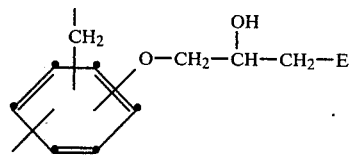 (g)

in which the radical E has the formula IX, and has an average molecular weight of between 1,000 and 100,000.

Some of the light-sensitive polymers containing groups of the formula IX can be prepared, for example, by reacting a polymer containing free —OH groups, preferably a synthetic resin of the novolac, phenoxy resin or phenolformaldehyde resin type, with a compound of the formula XI

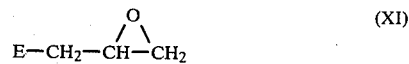 (XI)

in which E has the formula IX.

However, it is also possible to follow a procedure in which a synthetic resin which contains glycidyl groups instead of the free -OH groups and is preferably of the novolac, phenoxy resin or phenol-formaldehyde resin type is reacted with a halogenoindenonecarboxylic acid of the formula E-H, in which the radical E is the group of the formula IX.

The preferred polymers which contain structural elements of the formula g can also be prepared by both procedures.

The polymers which contain the groups of the formula IX in molecule chain members of the formulae a and b can be prepared by reacting a homopolymer or a copolymer of maleic anhydride, which polymer contains a substituted or unsubstituted maleic anhydride as a polymerised component, all or some of the anhydride groups being retained, with one of the compounds of the formulae XII and XIII

$E—(CH_2)_m—OH$     (XII)

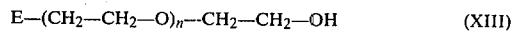

$E—(CH_2—CH_2—O)_n—CH_2—CH_2—OH$     (XIII)

in which m is a number from 2 to 6 and n is a number from 1 to 10 and in which E has the formula IX.

However, these last-mentioned polymers or similar polymers can also be prepared by reacting maleic anhydride, which can be substituted, with one of the compounds of the formulae (XII) or (XIII) in a first reaction and, in a 2nd reaction, polymerising the particular resulting unsaturated monomer, if desired together with other comonomers which contain at least one C=C double bond.

Maleic anhydride is preferably used as the starting substance for these polymers. In principle, however, it is also possible correspondingly to prepare polymers which are derived from substituted maleic anhydrides. The latter are in particular maleic anhydrides substituted by methyl. Suitable comonomers for maleic anhydride are, for example, styrene, vinyl ethers, ethylene and propylene.

The polymers which contain the groups of the formula IX in molecule chain members of the formulae c to e can be prepared by polymerising one or more of the compounds of the formulae XIV to XVI

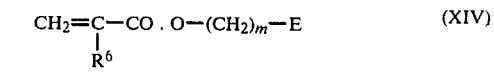  (XIV)

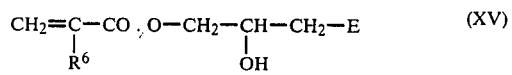  (XV)

$$CH_2=CH-O-CH_2-CH_2-E \quad (XVI)$$

in which $R^6$ is H or $CH_3$ and m and E are as defined for formula a, if desired together with further comonomers.

Suitable comonomers for the monomers of the formulae XIV to XVI are, for example, acrylates and methacrylates which do not contain the radical E, styrene and vinyl compounds, such as vinyl ethers, vinyl chloride and vinyl acetate and vinylidene chloride.

The polymers containing molecule chain members of the formula c can, however, also be prepared by subjecting a polyacrylic acid chloride or a polymethacrylic acid chloride, or a corresponding copolymer to a condensation reaction with, in each case, an ester of the formula E-$(CH_2)_m$-OH, in which E is the group of the formula IX and m is a number from 2 to 6. In this context, copolymers are to be understood as meaning those which contain the same comonomers as have been mentioned for the monomers of the formulae XIV to XVI.

The polymers containing molecule chain members of the formula d can also be prepared by reacting polyacrylic acid glycidyl esters or polymethacrylic acid glycidyl esters, or corresponding copolymers containing monomers free from glycidyl groups, with halogenoindenonecarboxylic acids of the formula E-H.

After the particular reaction has ended, the polymer can be precipitated by pouring the mixture into suitable organic solvents, for example aliphatic hydrocarbons, alcohols or dialkyl ethers, such as n-pentane, n-hexane, methanol, ethanol and diethyl ether. The polymer is then in the form of an orange-coloured product.

The photocrosslinkable polymers are suitable, for example, for the production of printing plates for the offset printing process, and for the preparation of photo-offset lacquers, for unconventional photography, for staining polymer images, which are visible after exposure and developing, with suitable dyes, such as oil-soluble dyes or, if the polymer contains acid groups, such as carboxylic acid groups or sulfonic acid groups, cationic dyes. The polymers are used in particular as so-called photoresists for the production of printed circuits by methods known per se.

PREPARATION EXAMPLES

Example 1

A mixture consisting of 88 g of powdered, anhydrous $AlCl_3$, 16 g of NaCl, 5.4 g of KCl and 16.7 g (0.1 mol) of dichloromaleic anhydride is initially introduced into a stirred flask provided with a HCl outlet and is heated at 90°–100° C. for a short time (until it has melted). 10.6 g (0.1 mol) of m-xylene are added at 70°–75° C. in the course of 45 minutes. After stirring for a further 30 minutes at 75°–80° C., the melt is introduced into a mixture of 25 ml of concentrated hydrochloric acid, water and ice (final volume about 1 liter) and the product is filtered off. After washing with water and drying in vacuo at 60° C., 23.0 g (97% of theory) of yellow-orange 1-oxo-2-chloro-5,7-dimethyl-indene-3-carboxylic acid are obtained. According to the thin layer chromatogram, the product contains only slight impurities and can therefore be used direct for further reactions. When recrystallised from ethyl acetate, the product melts at 255°–256° C.

$^1$H-NMR spectrum (100 mHz, δ values in ppm, solution in $(CD_3)_2SO$): 2.27 (S, 3H, -$CH_3$); 2.38 (S, 3H, -$CH_3$); 6.8 and 7.2 (2H, aromatic); about 13.5 (broad signal, 1H, $D_2O$ exchangeable).

The chemical analysis and the $^1$H-NMR spectrum correspond to the formula

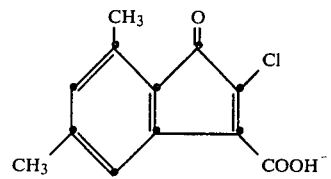

The indenones listed in the following table were prepared analogously.

| Example No. | Compound of the formula b | R³ | Introduction of the compound of the formula b into the melts | | Reaction after introduction of the compound of the formula b | | Compound of formula a | Yield % of theory | Recrystallised from | Melting point |
|---|---|---|---|---|---|---|---|---|---|---|
| | | | Time hours | Temperature °C. | Time hours | Temperature °C. | | | | |
| 2 | m-xylene | R³ = Br | 1 | 70–75 | 0.5 | 75–80 | ![structure with CH₃, CH₃, Br, COOH] | 79 | ethyl acetate | 257 |
| 3 | benzene | R³ = Cl | 0.75 | 70–75 | 2 | 80–85 | ![structure with Cl, COOH] | 90 | water + ethanol (1:1) | 228 |
| 4 | toluene | R³ = Cl | 0.75 | 70–75 | 1.5 | 80–85 | ![structure with CH₃, Cl, COOH] | 91 | ethyl acetate | 239 |

-continued

| Example No. | Compound of the formula b | $R^3$ (formula b structure) | Introduction of the compound of the formula b into the melts Time hours | Temperature °C. | Reaction after introduction of the compound of the formula b Time hours | Temperature °C. | Compound of formula a | Yield % of theory | Recrystallised from | Melting point |
|---|---|---|---|---|---|---|---|---|---|---|
| 5 | p-xylene | $R^3$ = Cl | 0.75 | 70–75 | 2 | 80–85 | (CH₃, CH₃-substituted chloroindenone carboxylic acid) | 88 | chlorobenzene | 170 |
| 6 | (indane) | $R^3$ = Cl | 1 | 70–75 | 1 | 75–80 | (fused ring chloroindenone carboxylic acid) | 95 | toluene | 239 |
| 7 | monochlorobenzene | $R^3$ = Cl | 1 | 80–85 | 2.5 | 95–100 | (Cl-substituted chloroindenone carboxylic acid) | 55 | ethyl acetate | 258 |
| 8 | 1,2,3-trimethylbenzene | $R^3$ = Cl | 1 | 75–80 | 0.5 | 75–80 | (trimethyl chloroindenone carboxylic acid) | 95 | glacial acetic acid | 225 |
| 9 | 1,2,4-trimethylbenzene | $R^3$ = Cl | 1 | 75–80 | 0.5 | 75–80 | (trimethyl chloroindenone carboxylic acid) | 97 | toluene | 193 |
| 10 | n-butylbenzene | $R^3$ = Cl | 0.75 | 75–80 | 1 | 80–85 | (n-butyl chloroindenone carboxylic acid) | 98 | cyclohexane | 157 |
| 11 | ethylbenzene | $R^3$ = Cl | 0.5 | 95–100 | 0.5 | 95–100 | (ethyl chloroindenone carboxylic acid) | 99 | cyclohexane | 150 |

EXAMPLE 12

A mixture consisting of 53 g of powdered, anhydrous AlCl₃ and 16.7 g (0.1 mol) of dichloromaleic anhydride in 80 ml of 1,2-dichloroethane is initially introduced into a stirred flask with a HCl outlet. 7.8 g (0.1 mol) of benzene are then added at 20°–30° C. in the course of about 30 minutes and the mixture is stirred at the indicated temperature until the thin layer chromatogram of a sample indicates complete conversion. The reaction mixture is then introduced into a mixture of 25 ml of concentrated hydrochloric acid, water and ice (final volume about 600 ml) and the dichloroethane solution is evaporated to dryness in vacuo. This yields 23.5 g of β-benzoyldichloroacrylic acid, which is cyclised under conditions analogous to those for the preparation of the chloroindenonecarboxylic acid by the 1-stage process according to Example 3, i.e. in the presence of the same flux mixture and using the same temperatures.

Yield 17.0 g, corresponding to 82% of theory. Melting point: 228° C.

The other halogeno-indenonecarboxylic acids of Examples 1 and 2 and 4 to 9 can be prepared analogously by this two-stage process.

The same end products are obtained when, in the above examples, an acid chloride of the formula $$\text{CH}_3\text{OOC}\diagdown\phantom{xx}\diagup\text{COCl}$$
$$R^3\diagup\phantom{xxx}\diagdown R^3$$

$R^3$=Cl or Br is used in place of dichloro- or dibromomaleic anhydride, in an equimolecular amount.

EXAMPLE 13

7.8 g (0.1 mol) of benzene are reacted with dichloromaleic anhydride in the presence of AlCl₃, in accordance with Example 12, and the resulting brown reaction solution is filtered (without decomposition with dilute hydrochloric acid) to remove a little AlCl₃ which has not dissolved. The filtrate is evaporated to dryness in vacuo in a rotary evaporator. The residue is heated at 150° C. for 30 minutes, during which time it disintegrates to a powder. After the customary working up by introducing into dilute hydrochloric acid, isolating and drying, a crude product is obtained and this is freed from the sparingly soluble dark by-product by recrystallisation from chlorobenzene. This yields 6.2 g, corresponding to 30% of theory, of 1-oxo-2-chloroindene-3-carboxylic acid.

EXAMPLE 14

14.6 g (0.2 mol) of dimethylformamide are initially introduced into a stirred flask with a HCl outlet and 54 g (0.4 mol) of powdered, anhydrous AlCl₃ and 16.7 g (0.1 mol) of dichloromaleic anhydride are introduced slowly, the temperature being kept below about 80° C. by cooling. 10.6 g (0.1 mol) of m-xylene are added at 70°-75° C. in the course of 45 minutes and the dark melt is stirred for 1.5 hours at 75°-80° C. Subsequent working up is carried out as described in Example 1. This yields 22.9 g, corresponding to 97% of theory, of 1-oxo-2-chloro-5,7-dimethylindene-3-carboxylic acid, which according to chromatography is approximately pure.

The halogenoindenone-carboxylic acids described in Examples 2 to 9 can be prepared analogously. In these cases, the reaction temperatures indicated in the particular examples are used. The reaction time (after the introduction of the compound of the formula) (II)) is increased to three times the indicated period.

EXAMPLE 15

54 g of powdered, anhydrous AlCl₃ and 10.6 g (0.1 mol) of m-xylene in 70 ml of 1,1,2,2-tetrachloroethane are initially introduced into a stirred flask with a HCl outlet. 17.8 g (0.1 mol) of dichloromaleic anhydride are then added in the course of about 30 minutes and the mixture is stirred at 20°-30° C. for 2 hours. The mixture is then kept at a temperature of 55°-60° C. for 10 hours and poured into ice-water which contains 25 ml of concentrated hydrochloric acid. The tetrachloroethane solution is separated off, about 250 ml of water are added and the solvent is distilled off in vacuo in a rotary evaporator. The product is filtered off, washed with a little water and dissolved at room temperature in 800 ml of water with the addition of the necessary amount of sodium carbonate. After separating off an insoluble impurity by filtration, excess hydrochloric acid is added to the filtrate and the product which has precipitated is isolated in the customary manner. This yields 20.5 g (87% of theory) of 1-oxo-2-chloro-5,7-dimethyl-indene-3-carboxylic acid, the characteristics of which correspond to those described in Example 1.

EXAMPLES 16 TO 18

The following compounds are prepared analogously: 1-oxo-2-chloro-5,6-dimethylindene-3-carboxylic acid, 98% of theory, melting point 229° (recrystallised from glacial acetic acid), using o-xylene. The product corresponding to Example 5 is obtained from p-xylene, and 1-oxo-2-chloro-4,5,7-trimethylindene-3-carboxylic acid with a melting point of 194° (recrystallised from toluene) is obtained from 1,2,4-trimethylbenzene.

EXAMPLE 19

71 g (0.3 mol) of 1-oxo-2-chloro-5,7-dimethylindene-3-carboxylic acid are suspended in 400 ml of ethylene glycol dimethyl ether and 250 ml of ethylene glycol. 70 ml of concentrated sulfuric acid are added, with stirring, and the mixture is kept at a temperature of 55°-60° for 48 hours. The reaction mixture is introduced into ice-water and the resulting mixture is filtered. The residue on the suction filter is suspended in 2 liters of water, the pH of the suspension is adjusted to 8 with sodium carbonate and the suspension is filtered and the material on the filter is washed with 500 ml of water. After drying, 42 g of the ester of the formula

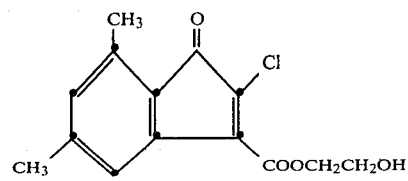

are obtained: melting point 112° (recrystallised from toluene).

22 g of carboxylic acid which has not been esterified can be recovered from the alkaline filtrate containing sodium carbonate, by precipitating with hydrochloric acid, and can be re-used.

EXAMPLE 20

The 2-chloro-indenonecarboxylic acid ester of the formula

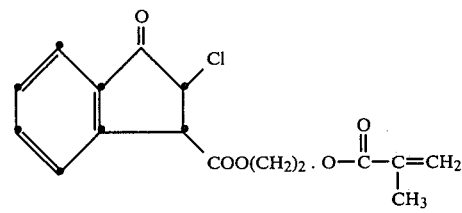

2.0 g (0.03 mol) of 2-hydroxy-ethyl chloroindenonecarboxylate are dissolved in 20 ml of dry methylene chloride. 3 g (0.03 mol) of sodium carbonate are added to this solution. A solution of 3.5 g (0.033 mol) of methacrylic acid chloride in 5 ml of dry methylene chloride is added dropwise to this mixture. After the reaction has taken place, the solution is filtered to remove the sodium chloride formed and sodium carbonate.

The filtrate is washed until neutral and is then evaporated to dryness in a rotary evaporator. Yield of the ester: 84% of theory.

Melting point: 98°-100° C.

NMR(CDCl₃): 2.0 ppm [3H], 2.6 ppm [4H] 5.6 and 6.2 ppm [2H], 7.1-7.8 ppm [4H]

Elementary analysis: calculated 59.92% C, 4.09% H, 11.05% Cl: found: 59.86% C, 4.03% H, 11.27% Cl, C₁₆H₁₃O₅Cl (320.73).

Use Examples

Example I 2.5 g of a copolymer of methyl methacrylate and glycidyl methacrylate [(molar ratio 1:1), $\overline{M}w$ 60,000] are dissolved together with 1.8 g (8.63 mmols) of chloroindenonecarboxylic acid and 0.01 g of tetramethylammonium chloride in 20 g of cyclohexanone. This solution is heated at 120° C. for about 2 hours. After cooling to room temperature, the solution is filtered. The filtrate can be used direct as a coating solution for the preparation of photolacquer coatings.

In addition to structural elements of the formula

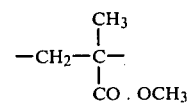

the resulting polymer contains structural elements of the formula

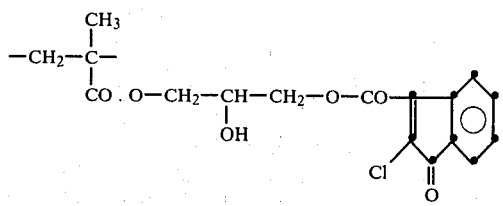

Like all of the polymers described in the examples which follow, it is orange-coloured.

Example II 10 g of a copolymer of methyl vinyl ether and maleic anhydride (molar ratio 1:1 alternating, Mw 740,000), 8 g (0.03 mol) of 2-hydroxyethyl chloroindenonecarboxylate and 0.15 ml of concentrated sulfuric acid are dissolved in 120 ml of dry tetrahydrofuran. The solution is refluxed for 24 hours under nitrogen. The solution is then cooled to room temperature and filtered. The filtrate can be used direct for coating purposes.

In order to determine the composition, a small sample of the filtrate is precipitated in ether.

Elementary analysis: calculated: 55.27% C, 4.46% H, 6.28% Cl: found: 55.85% C, 4.59% H, 5.56% Cl.

Example III 2.66 g of a copolymer of ethylene and maleic anhydride (1:1 alternating, $\overline{M}w$ 100,000) and 5.34 g (0.020 mol) of 2-hydroxyethyl chloroindenonecarboxylate are dissolved in 40 ml of dry N-methylpyrrolidone. This solution is boiled at 100° C. for 48 hours. After cooling to room temperature, it is filtered. The filtrate can be used direct for coating purposes. A sample is precipitated in ether and the intrinsic viscosity number of the product is determined. ($\eta$ intr) (dimethylformamide, 20° C.): 0.3 dl/g.

Example IV

The procedure is analogous to that of Example I. The starting polymer used is Gantrez 119 AN$^R$. It is a product marketed by the GAF Corporation, U.S.A. and specifically is a copolymer of vinyl methyl ether and maleic anhydride and has a Mw of approximately 740,000. The chloroindenone acid derivative used is 2-hydroxyethyl chloroindenonecarboxylate. The weight ratio of these reactants is 2:5.

A light-sensitive polymer with an intrinsic viscosity number ($\eta$ intr.) of 0.25 dl/g (dimethylformamide; 20° C.) results.

Example V

The procedure is analogous to that of Example IV except that 2-hydroxy-ethyl 2-chloro-5,7-dimethylindenonecarboxylate is used in place of 2-hydroxyethyl chloro-indenonecarboxylate and that the weight ratio of the reactants is 2:2.32 instead of 2:5. A photocrosslinkable polymer with a $\eta$ intr. of 0.22 dl/g (dimethylformamide; 20° C.) results.

Example VI 10.45 g of polymethacrylic acid chloride ($\overline{M}w$ 40,000), dissolved in 10 ml of dry toluene, are dissolved, together with 12.9 g (0.05 mol) of 2-hydroxyethyl chloroindenonecarboxylate, in 80 ml of chlorobenzene. 10 g of finely powdered 3 Å molecular sieve are added to this solution. This solution is refluxed for about 2 hours. After cooling to room temperature, the reaction solution is filtered and the filtrate is then precipitated in 2 l of methanol. After drying, the resulting pale powder has an intrinsic viscosity number $\eta$ intr. (dimethylformamide, 20° C.) of 0.1 dl/g.

Example VIII

The coating solution prepared according to Example I is used to coat copper-laminated epoxy laminates:

Copper-laminated epoxy sheets are coated with the abovementioned polymer solution using a coating centrifuge. After drying, an approximately 5 μm thick polymer film is obtained on the copper surface. The dry sheet coated in this way is exposed for 3 minutes through a line negative to UV light (wavelength above 320 nm); light source: 400 watt high-pressure mercury vapour lamp; distance 50 cm. After exposure, the resulting image is already visible and the parts which have not been exposed are dissolved out by developing in cyclohexanone. The copper which has been uncovered is dissolved out by etching with iron-III chloride and a copper image corresponding to the line negative is obtained.

Example VIII

The coating solution prepared according to Example IV is used to coat aluminium films:

The aluminium film is coated with the above-mentioned polymer solution using a coating centrifuge and is then dried. After drying, an approximately 5 μm thick polymer film is obtained on the aluminium support. The plate coated in this way is exposed for 1 minute through a line negative to UV light (wavelength above 320 nm, light source: 400 watt high-pressure mercury vapour lamp, distance 50 cm). After exposure, the resulting image is already visible and the parts which have not been exposed are dissolved out by developing in 5% sodium bicarbonate solution. The resulting relief image can be rendered more intense by means of cationic dyes, for example Maxilon red. The coloured image of the negative original forms.

What is claimed is:

1. A process for the preparation of an indenonecarboxylic acid of the formula I

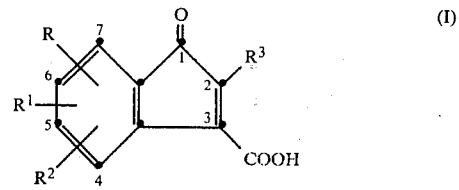

in which $R^3$ is Cl or Br, and R, $R^1$ and $R^2$ are identical or different and R is a n-alkyl radical having 1 to 4 C atoms, or is H, Cl, Br or F, $R^1$ is a n-alkyl radical having 1 to 4 C atoms, or is H, and $R^2$ is H or $CH_3$, or $R^1$ and $R^2$ together are the group $-CH_2CH_2CH_2-$, in which latter case the bond to the six-membered ring is via the C atoms in the 5-position and 6-position of the nucleus, which comprises subjecting an aromatic compound of the formula II

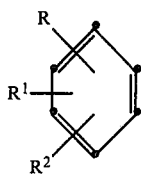

in which the H atoms on at least 2 adjacent C atoms of the nucleus have not been replaced by substituents and in which R, $R^1$ and $R^2$ are as defined for formula I, either together with a diahalogenomaleic anhydride of the formula III

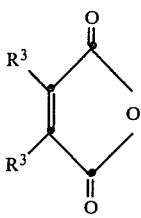

or together with an ester of the formula IV

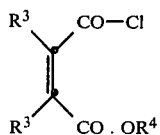

in which formulae $R^3$ is as defined for formula I and $R^4$ is in each case a low-molecular aliphatic radical, a cycloaliphatic radical, an aliphatic-aromatic radical or an aromatic radical, in each case in an approximately stoichiometric ratio, to a condensation reaction in the presence of $AlCl_3$ and if desired in the presence of inert fluxes and/or solvents, at temperatures between 40° and 150° C., and hydrolysing the reaction product thus obtained.

2. A process according to claim 1, wherein the condensation reaction is carried out in 2 stages by preparing a keto-carboxylic acid of the formula V

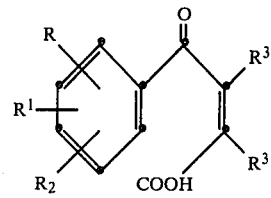

in the reaction mixture in the 1st stage, in a manner known per se, and isolating this acid and, in the 2nd stage, cyclising the ketoacid of the formula V, likewise in the presence of $AlCl_3$ and if desired in the presence of inert fluxes and/or solvents, but at temperatures between 40° and 150° C., to give the corresponding indenonecarboxylic acid of the formula I, which is liberated from the resulting reaction mixture by hydrolysis.

3. A process according to claim 1, wherein a dihalogenomaleic anhydride or ester of the formula III or IV is used in which $R^3$ is chlorine.

4. A process according to claim 1, wherein an ester of the formula IV is used in which $R^4$ is an aliphatic radical having a total of 1 to 4 C atoms.

5. A process according to claim 1, wherein $AlCl_3$ is used in an amount of at least 1 mol per mol of the dihalogenomaleic anhydride of the formula III or of the ester of the formula IV.

6. A process according to claim 1, wherein the condensation reaction is carried out in the presence of an inert solvent.

7. A process according to claim 6, wherein the condensation reaction is carried out in the presence of a dialkylamide of a low-molecular carboxylic acid as the solvent, the molar ratio of dialkylamide to $AlCl_3$ being at least 1:1.

8. A process according to claim 1, wherein the condensation reaction is allowed to proceed in the presence of inert fluxes, the amounts being such that the melting point which results when the fluxes are mixed with the $AlCl_3$ in the reaction mixture is lower than the reaction temperature.

9. A process according to claim 8, wherein the fluxes used are inorganic salts or organic fluxes or mixtures of the salts with the organic fluxes, the amounts being such that a lowering of the melting point of the salt mixture results when the fluxes are mixed with the $AlCl_3$ in the reaction mixture.

10. A process according to claim 9, wherein the organic fluxes used are dialkylamides of low-molecular carboxylic acids, the molar ratio of dialkylamide to $AlCl_3$ being within the limits 1:4 to 1:1.

11. A process according to claim 9, wherein the inorganic salts employed are NaCl and/or KCl, if desired together with dimethylformamide as an organic flux.

* * * * *